US006261793B1

(12) United States Patent
Whyte et al.

(10) Patent No.: US 6,261,793 B1
(45) Date of Patent: Jul. 17, 2001

(54) RAS CONVERTING ENDOPROTEASE (RCE) AND METHODS

(75) Inventors: David Whyte, Belmont, CA (US); Marnie McGuirk, Marlboro, NJ (US); Irma Nuñez-Oliva, North Bergen, NJ (US); Tish Hockenberry, Kenilworth, NJ (US); James Pai, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/262,749

(22) Filed: Mar. 4, 1999

(51) Int. Cl.[7] .............................. C12Q 1/48; C12N 9/10; G01N 33/48; C07K 14/435
(52) U.S. Cl. .............................. 435/15; 435/193; 435/4; 436/63; 436/64; 530/350
(58) Field of Search .............................. 435/4, 6, 15, 193; 530/350; 436/63, 64

(56) References Cited

U.S. PATENT DOCUMENTS 5,932,432 * 8/1999 Crowell et al. .

FOREIGN PATENT DOCUMENTS

| 0887415 | * | 12/1998 | (EP) . |
| WO 98/54333 | * | 12/1998 | (WO) . |
| WO 99/14343 | * | 3/1999 | (WO) . |

OTHER PUBLICATIONS

Burgess, W.H. et al. Possible dissociation of the heparin-–binding and mitogenic activities of heparin–binding (acidic fibroblast) growth factor–1 from its receptor–binding activities by site–directed mutagenesis of a single lysine residue. J. Cell Biolo, 1990.*

Structure–function relationships in glucagon: Properties of highly purified des–his1–, monoiodo–, and [des–Asn28, Thr29](homoserine lactone27)–glucagon. Biochemistry, 14(8): 1559–1563, 1975.*

Lazar, E. et al. Transforming growth factor alpha: mutation of aspartic acid 47 and leucine 48 results in different biological activities. Mol. Cell. Biology, 8(3): 1247–1252, 1988.*

Boyartchuk, V.L., et al., (1997), Modulation of Ras and a–Factor Function by Carboxyl–Terminal Proteolysis, *Science* vol. 275, pp. 1796–1800.

Schmidt, W. K., et al., (1998), Endoplasmic reticulum membrane localization of Rce1p and Ste24p, yeast proteases involved in carboxy–terminal CAAX protein processing and amino–terminal a–factor cleavage, *Proc. Natl. Acad. Sci., USA*, vol. 95, pp. 11175–11180.

* cited by examiner

*Primary Examiner*—Anthony C. Caputa
*Assistant Examiner*—Anne L. Holleran
(74) *Attorney, Agent, or Firm*—Immac J. Thampoe; Jaye McLaughlin

(57) ABSTRACT

The present invention provides human ras converting endoprotease (RCE), the encoding nucleic acids, recombinant vectors, transformed host cells and methods of making human RCE. More particularly, the invention provides methods of using human RCE in screening systems to identify inhibitors of human RCE useful for the treatment of various medical conditions. This invention further relates to inhibitors of human RCE.

2 Claims, No Drawings

RAS CONVERTING ENDOPROTEASE (RCE) AND METHODS

TECHNICAL FIELD

The present invention relates to human ras converting endoprotease (RCE). More particularly, it relates to methods of using human RCE in screening systems to identify inhibitors of human RCE useful for the treatment of various medical conditions. This invention further relates to inhibitors of human RCE.

BACKGROUND OF THE INVENTION

Mutations in Ras proteins are found in more than 30% of all human cancers, including greater than 90% of pancreatic cancers, 50% of colon cancers and 30% of lung adenocarcinoma. Ras genes encode a family of guanine nucleotide-binding proteins that, to be functional, must be associated with the inner surface of the plasma membrane. Ras proteins lack the conventional transmembrane or hydrophobic sequences associated with other membrane-associated proteins and are initially synthesized as soluble, cytoplasmic proteins. Their membrane association is triggered by a series of post-translational processing steps involving a carboxy terminal motif referred to as the CaaX box. The CaaX box consists of a conserved cysteine residue, two aliphatic amino acids, and a carboxy-terminal amino acid residue. The post-translational steps required for the attachment of Ras proteins to the inner plasma membrane are: (i) the transfer of farnesyl pyrophosphate (a 15-carbon isoprene lipid) or geranylgeranyl moiety (a four-isoprene unit molecule) onto the cysteine in the carboxy terminal "CaaX" motif by a prenyl transferase i.e., farnesyl protein transferase (FPT) or geranylgeranyl protein transferase (GGPT); (ii) proteolytic cleavage of the three carboxy terminal amino acid residues by Ras Converting Endoprotease (RCE); and(iii) methylation of the resulting carboxy terminal prenyl cysteine residue by prenyl cysteine specific Carboxymethyltransferase (PC-CMT).

Cleavage by RCE modulates Ras function in yeast, therefore it may be a novel target to modulate oncogenic Ras in human tumors. Null mutations in RCE cause no obvious growth or viable defects, whereas mutations in FPT cause cells to be either growth defective or dead. If these results in yeast translate to human cells, inhibitors of RCE may be safer therapeutic agents than inhibitors of FPT.

Accordingly, the identification of human RCE will provide a critical tool necessary for the development of inhibitors of RCE which represent novel therapeutic agents for the treatment of human cancers.

SUMMARY OF THE INVENTION

The present invention provides human ras converting endopeptidase (RCE) having the amino acid sequence of SEQ ID NO: 2. Also provided are isolated nucleic acids encoding human RCE.

In addition, this invention provides methods of identifying inhibitors of human RCE comprising:
(a) contacting a prenylated protein, wherein one or more of the three carboxy terminal amino acid residues of the prenylated protein is radiolabeled, with a sample to be tested for the presence of a RCE inhibitor, and with human RCE having the amino acid sequence of SEQ ID NO: 2; and
(b) measuring the amount of labeled tripeptide released. whereby the human RCE inhibitor in the sample is identified by measuring the amount of labeled tripeptide released, compared to what would be measured in the absence of such inhibitor.

Also provided are methods of identifying inhibitors of human RCE comprising:
(a) contacting a prenylated peptide with: (i) a sample to be tested for the presence of a RCE inhibitor; (ii) human RCE having the amino acid sequence of SEQ ID NO: 2; (iii) prenyl cysteine specific carboxymethyltransferase; and (iv) a radiolabeled methyl group donor; and
(b) measuring the amount of the radiolabeled methyl group incorporated into the carboxy terminal of the prenylated peptide
whereby the human RCE inhibitor in the sample is identified by measuring the reduction in the amount of radiolabeled methyl group incorporated into the prenylated peptide, compared to what would be measured in the absence of such inhibitor.

In a preferred embodiment, membranes isolated from cells expressing a nucleic acid encoding human RCE are used as the source of human RCE.

The present invention also contemplates molecules that specifically inhibit the activity of human RCE. Such molecules include small organic molecules, peptides, and antibodies or antigen binding fragments of antibodies which specifically inhibit human RCE activity. In a preferred embodiment the human RCE inhibitors are orally active, small organic molecules.

This invention also contemplates pharmaceutical compositions, for use in treating human cancers, comprising: (a) an effective amount of a human RCE inhibitor; and (b) a pharmaceutically acceptable carrier.

This invention further provides a method for treating human cancers comprising administering to a subject afflicted with cancer a pharmaceutical composition comprising: (a) an effective amount of a human RCE inhibitor; and (b) a pharmaceutically acceptable carrier.

This invention also provides anti-sense oligonucleotides capable of specifically hybridizing to mRNA encoding human RCE having the amino acid sequence defined by SEQ ID NO: 2 so as to prevent translation of the mRNA. Additionally, this invention provides anti-sense oligonucleotides capable of specifically hybridizing to the genomic DNA molecule encoding human RCE having an amino acid sequence defined by SEQ ID NO: 2.

DESCRIPTION OF THE INVENTION

All references cited herein are hereby incorporated in their entirety by reference.

Cloning of Human Ras Converting Endoprotease

Yeast RCE1 amino acid sequence was used to query dbEST databases. Partial cDNAs for the human homolog of yeast RCE was found from dbEST [W96411 (p=2e-19); human and AA168614 (p=2e-20); mouse]. We obtained a human RCE homolog clone (358628) from the IMAGE Consortium, and sequenced it to confirm its homology to yeast RCE.

Northern analysis was performed to determine tissue distribution of human RCE using IMAGE clone 358628 as the probe. RCE expression appeared highest in placenta, with a transcript size of approximately 2.0 Kb. A human placenta phage library was screened to obtain a full length clone of human RCE. Six positive clones were found. Sequencing of these clones confirmed their homology to yeast RCE, IMAGE clone 358628, and to each other.

One of the positive clones, designated hRCE-7, was chosen for use in cloning and expression studies due to the presence of a start codon at the 5' end, a coding region containing a stop codon, and a 3' untranslated region including a poly $A^+$ tail. To demonstrate expression of human RCE, hRCE-7 was cloned into mammalian, bacterial, and yeast expression vectors. Epitope tags were cloned onto the amino and carboxy terminals of hRCE-7 for Western detection. The construct pDD1-hRCE containing the coding region of hRCE-7 with a 5' S-tag in a yeast expression vector was used to transform a yeast Rce/Afc double knock out, and the resulting yeast clone (136B) was positive in both the Halo and biochemical assays.

The nucleotide sequence of the complete open reading frame and the corresponding amino acid sequence of human RCE cDNA cloned from the human placental cDNA library are defined in the Sequence Listing by SEQ ID NO: 1 and SEQ ID NO: 2, respectively.

Protein Purification

The proteins, polypeptides and fragments of this invention can be purified by standard methods, including but not limited to salt or alcohol precipitation, preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in *Guide to Protein Purification, Methods in Enzymology*, Vol. 182, M. Deutscher, Ed., 1990, Academic Press, New York, N.Y.

Nucleic Acids and Expression Vectors

As used herein, the term "isolated nucleic acid" means a nucleic acid such as an RNA or DNA molecule, or a mixed polymer, which is substantially separated from other components that are normally found in cells or in recombinant DNA expression systems. These components include but are not limited to ribosomes, polymerases, serum components, and flanking genomic sequences. The term thus embraces a nucleic acid which has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules but may, in some embodiments, contain minor heterogeneity. Such heterogeneity is typically found at the ends of nucleic acid coding sequences or in regions not critical to a desired biological function or activity.

A "recombinant nucleic acid" is defined either by its method of production or structure. Some recombinant nucleic acids are thus made by the use of recombinant DNA techniques which involve human intervention, either in manipulation or selection. Others are made by fusing two fragments not naturally contiguous to each other. Engineered vectors are encompassed, as well as nucleic acids comprising sequences derived using any synthetic oligonucleotide process.

For example, a wild-type codon may be replaced with a redundant codon encoding the same amino acid residue or a conservative substitution, while at the same time introducing or removing a nucleic acid sequence recognition site. Similarly, nucleic acid segments encoding desired functions may be fused to generate a single genetic entity encoding a desired combination of functions not found together in nature. Although restriction enzyme recognition sites are often the target of such artificial manipulations, other site-specific targets, e.g., promoters, DNA replication sites, regulation sequences, control sequences, or other useful features may be incorporated by design. Sequences encoding epitope tags for detection or purification as described above may also be incorporated.

A nucleic acid "fragment" is defined herein as a nucleotide sequence comprising at least about 17, generally at least about 25, preferably at least about 35, more preferably at least about 45, and most preferably at least about 55 or more contiguous nucleotides.

The nucleic acids of the invention may be operably linked to DNA segments which control transcription, translation, and DNA replication.

The term "substantially pure" is defined herein to mean a protein, nucleic acid or other material that is free from other contaminating proteins, nucleic acids, and other biologicals derived from an original source organism or recombinant DNA expression system. Purity may be assayed by standard methods and will typically exceed at least about 50%, preferably at least about 75%, more preferably at least about 90%, and most preferably at least about 95% purity. Purity evaluation may be made on a mass or molar basis.

Nucleic acids encoding human RCE can be prepared by standard methods. For example, DNA can be chemically synthesized using, e.g., the phosphoramidite solid support method of Matteucci et al. [*J. Am. Chem. Soc.* 103:3185 (1981)], the method of Yoo et al. [*J. Biol. Chem.* 764:17078 (1989)], or other well known methods. This can be done by sequentially linking a series of oligonucleotide cassettes comprising pairs of synthetic oligonucleotides, as described below.

Of course, due to the degeneracy of the genetic code, many different nucleotide sequences can encode human RCE. The codons can be selected for optimal expression in prokaryotic or eukaryotic systems. Such degenerate variants are of course also encompassed by this invention.

Moreover, nucleic acids encoding human RCE can readily be modified by nucleotide substitutions, nucleotide deletions, nucleotide insertions, and inversions of nucleotide stretches. Such modifications result in novel DNA sequences which encode proteins having immunogenic or antigenic activity in common with the wild-type enzyme. These modified sequences can be used to produce wild-type or mutant enzymes, or to enhance expression in a recombinant DNA system.

Insertion of the DNAs encoding human RCE into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, desired sites may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., *Science* 239:487 (1988). The cleaved vector and the DNA fragments may also be modified if required by homopolymeric tailing.

Recombinant expression vectors used in this invention are typically self-replicating DNA or RNA constructs comprising nucleic acids encoding human RCE, usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also may contain an origin of replication that allows the vector to replicate independently of the host cell.

Vectors that could be used in this invention include microbial plasmids, viruses, bacteriophage, integratable DNA fragments, and other vehicles which may facilitate integration of the nucleic acids into the genome of the host. Plasmids are the most commonly used form of vector but all other forms of vectors which serve an equivalent function and which are, or become, known in the art are suitable for use herein. See, e.g., Pouwels et al., *Cloning Vectors: A Laboratory Manual,* 1985 and Supplements, Elsevier, N.Y., and Rodriguez et al. (eds.), *Vectors: A Survey of Molecular Cloning Vectors and Their Uses,* 1988, Buttersworth, Boston, Mass.

Expression of nucleic acids encoding human RCE of this invention can be carried out by conventional methods in either prokaryotic or eukaryotic cells.

Prokaryotic expression control sequences typically used include promoters, including those derived from the β-lactamase and lactose promoter systems [Chang et al., *Nature* 198:1056 (1977)], the tryptophan (trp) promoter system [Goeddel et al., *Nucleic Acids Res.* 8:4057 (1980)], the lambda $P_L$ promoter system [Shimatake et al., *Nature* 292:128 (1981)] and the tac promoter [De Boer et al., *Proc. Natl. Acad. Sci. USA* 292:128 (1983)]. Numerous expression vectors containing such control sequences are known in the art and available commercially.

Suitable host cells for expressing nucleic acids encoding human RCE include prokaryotes and eukaryotes. These hosts may include strains of *E. coli*, Pseudomonas, Bacillus, Streptomyces, fungi, yeast, insect cells such as *Spodoptera frugiperda* (SF9), animal cells such as HeLa cells, Chinese hamster ovary (CHO) cell lines, baby rat kidney (BRK) cell lines, insect cell lines, bird cell lines, and monkey (COS) cell lines.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express human RCE include but are not limited to those containing the lac promoter (pUC-series); trp promoter (pBR322-trp); Ipp promoter (the pIN-series); lambda-pP or pR promoters (pOTS); or hybrid promoters such as ptac (pDR540). See Brosius et al., "Expression Vectors Employing Lambda-, trp-, lac-, and Ipp-derived Promoters", in Rodriguez and Denhardt (eds.) *Vectors: A Survey of Molecular Cloning Vectors and Their Uses,* 1988, Buttersworth, Boston, pp. 205–236.

Eukaryotic cells are preferred hosts for the recombinant production of human RCE. Transformation or transfection and propagation of such cells has become a routine procedure. Lower eukaryotic cells such as yeast are particularly useful for expressing the human RCE of this invention Expression vectors for such cells usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Yeast vectors typically use a strong yeast promoter such as the GAL4 promoter. Representative examples of suitable expression vectors for use in higher eukaryotic cells include pCR® 3.1, pCDNA1, pCD [Okayama et al., *Mol. Cell Biol.* 5:1136 (1985)], pMC1neo Poly-A [Thomas et al., *Cell* 51:503 (1987)], pUC19, pREP8, pSVSPORT and derivatives thereof, and baculovirus vectors such as pAC 373 or pAC 610. Examples of vectors suitable for use in lower eukaryotic cells, such as yeast include pESC, pESP-1, pESP-2 and pESP-3.

Screening Systems and Methods

The human RCE of this invention can be employed in screening systems to identify inhibitors of human RCE. Essentially, these systems provide methods for bringing together human RCE, a substrate for human RCE, and a sample to be tested for the presence of a inhibitor of human RCE.

Two basic types of screening systems can be used, a direct assay or a coupled assay.

Generally, a nucleic acid encoding human RCE of the invention is transfected into an appropriate host cell, whereby the RCE will become incorporated into the membrane of the cell. A membrane fraction can then be isolated from the cell and used as a source of RCE for the assay.

In the basic form of the direct assay, the method for identifying a human RCE inhibitor comprises:

(a) contacting a prenylated peptide, wherein one or more of the three carboxy terminal amino acid residues of the prenylated peptide is radiolabeled, with a sample to be tested for the presence of a RCE inhibitor and with human RCE having the amino acid sequence of SEQ ID NO: 2; and (b) measuring the amount of labeled tripeptide released whereby the human RCE inhibitor in the sample is identified by measuring the amount of labeled tripeptide released, compared to what would be measured in the absence of such inhibitor.

In the basic form of the coupled assay, the method for identifying a human RCE inhibitor comprises:

(a) contacting a prenylated peptide with: (i) a sample to be tested for the presence of a RCE inhibitor; (ii) human RCE having the amino acid sequence of SEQ ID NO: 2; (iii) prenyl cysteine specific carboxymethyltransferase; and (iv) a radiolabeled methyl group donor; and (b) measuring the amount of the radiolabeled methyl group incorporated into the carboxy terminal of the prenylated peptide whereby the human RCE inhibitor in the sample is identified by measuring the reduction in the amount of radiolabeled methyl group incorporated into the prenylated peptide, compared to what would be measured in the absence of such inhibitor.

Pharmaceutical Compositions

The human RCE inhibitors of this invention such as, for example, small organic molecules, peptides, neutralizing antibodies or binding fragments thereof, as well as other types inhibitors, which can be identified using the methods of the invention, may be used therapeutically to inhibit the activity of RCE, and thereby to treat any medical condition caused or mediated by RCE. In a preferred embodiment the medical condition is cancer.

The dosage regimen involved in a therapeutic application will be determined by the attending physician, considering various factors which may modify the action of the human RCE inhibitor, e.g., the condition, body weight, sex and diet of the patient, the severity of any infection, time of administration, and other clinical factors.

Administration of the compositions of this invention is typically parenteral, by intraperitoneal, intravenous subcutaneous, or intramuscular injection, or by infusion or by any other acceptable systemic method. Administration by intravenous infusion, typically over a time course of about 1 to 5 hours, is preferred.

An "effective amount" of a composition of the invention is an amount that will ameliorate one or more of the well known parameters that characterize medical conditions caused or mediated by RCE. Many such parameters and conditions have been described, e.g., as in reviews by Bantfa (*Psychopharmacology: The Fourth Generation of Progress,* 1995, F. E. Bloom and D. J. Kupfer, Eds., Ravin Press, Ltd., New York, N.Y., pp. 563–571) and Crawley [*Life Science* 58:2185-2199 (1996)].

Although the compositions of this invention could be administered in simple solution, they are more typically used in combination with other materials such as carriers, preferably pharmaceutical carriers. Useful pharmaceutical carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. *Remington's Pharmaceutical Science,* 17th Ed. (Mack Publishing Company, Easton, Pa., 1990). Alternatively, compositions of the invention may be introduced into a patient's body by implantable drug delivery systems [Urquhart et al., *Ann. Rev. Pharmacol. Toxicol.* 24:199 (1984)].

Therapeutic formulations may be administered in many conventional dosage formulation. Formulations typically comprise at least one active ingredient, together with one or more pharmaceutically acceptable carriers. Formulations may include those suitable for oral, rectal, nasal, or parenteral (including subcutaneous, intramuscular, intravenous and intradermal) administration.

The formulations may conveniently be presented in unit dosage form and may be prepared by any methods well known in the art of pharmacy. See, e.g., Gilman et al. (eds.) (1990), *The Pharmacological Bases of Therapeutics,* 8th Ed., Pergamon Press; and *Remington's Pharmaceutical Sciences,* supra, Easton, Pa.; Avis et al. (eds.) (1993) *Pharmaceutical Dosage Forms: Parenteral Medications* Dekker, N.Y. York; Lieberman et al. (eds.) (1990) *Pharmaceutical Dosage Forms: Tablets* Dekker, N.Y.; and Lieberman et al. (eds.) (1990), *Pharmaceutical Dosage Forms: Disperse Systems* Dekker, N.Y.

For therapeutic use, the RCE antibodies and fragments are preferably chimeric or humanized to reduce antigenicity and human anti-mouse antibody (HAMA) reactions. The methodology involved is disclosed, e.g., in U.S. Pat. No. 4,816, 397 to Boss et al. and in U.S. Pat. No. 4,816,567 to Cabilly et al. Further refinements on antibody humanization are described in European Patent 451 216 B 1.

Typical protocols for the therapeutic administration of antibodies are well known in the art and have been disclosed, e.g., by Elliott et al. [*The Lancet* 344:1125 (1994)], Isaacs et al. [*The Lancet* 340:748 (1992)], Anasetti et al. [*Transplantation* 54:844 (1992)], Anasetti et al. [*Blood* 84:1320 (1994)], Hale et al. [*The Lancet* 2:1394 (Dec. 17, 1988)], Queen [*Scrip* 1881:18 (1993)] and Mathieson et al. [*N. Eng. J. Med.* 323:250 (1990)].

Anti-Sense Molecules

The present invention also encompasses anti-sense oligonucleotides capable of specifically hybridizing to mRNA encoding a human RCE having an amino acid sequence defined by SEQ ID NO: 2 so as to prevent translation of the mRNA. Additionally, this invention contemplates anti-sense oligonucleotides capable of specifically hybridizing to the genomic DNA molecule encoding a human RCE having the amino acid sequence defined by SEQ ID NO: 2.

This invention further provides pharmaceutical compositions comprising (a) an amount of an oligonucleotide effective to reduce activity of RCE by passing through a cell membrane and binding specifically with mRNA encoding the RCE in the cell so as to prevent its translation and (b) a pharmaceutically acceptable carrier capable of passing through a cell membrane. In an embodiment, the oligonucleotide is coupled to a substance which inactivates mRNA. In another embodiment, the substance which inactivates mRNA is a ribozyme.

Other Mammalian RCE

The present invention provides methods for cloning RCE from other mammalian species. Briefly, Southern and Northern blot analysis can be carried out to identify cells from other species expressing genes encoding RCE. Complementary DNA (cDNA) libraries can be prepared by standard methods from mRNA isolated from such cells, and degenerate probes or PCR primers based on the nucleic acid and amino acid sequences provided herein can be used to identify clones encoding RCE.

Alternatively, expression cloning methodology can be used to identify particular clones encoding RCE. An antibody preparation which exhibits cross-reactivity with RCE from a number of mammalian species may be useful in monitoring expression cloning. However identified, clones encoding RCE from various mammalian species can be isolated and sequenced, and the coding regions can be excised and inserted into an appropriate vector.

EXAMPLES

The present invention can be illustrated by the following examples. Unless otherwise indicated, percentages given below for solids in solid mixtures, liquids in liquids, and solids in liquids are on a wt/wt, vol/vol and wt/vol basis, respectively. Sterile conditions were generally maintained during cell culture.

Materials and General Methods

Standard methods were used, as described, e.g., in Maniatis et al., *Molecular Cloning: A Laboratory Manual,* 1982, Cold Spring Harbor Laboratory, Cold Spring Harbor Press; Sambrook et al., *Molecular Cloning: A Laboratory Manual,* (2d ed.), Vols 1–3, 1989, Cold Spring Harbor Press, N.Y.; Ausubel et al., *Biology,* Greene Publishing Associates, Brooklyn, N.Y; or Ausubel, et al. (1987 and Supplements), *Current Protocols in Molecular Biology,* Greene/Wiley, N.Y.; Innis et al. (eds.) *PCR Protocols: A Guide to Methods and Applications,* 1990, Academic Press, N.Y.

The polymerase chain reaction (PCR) was carried out using the Clontech protocols. Briefly, PCR was always run with KLENTAQ polymerase, which possesses proof reading activity (Clontech), and a cycling profile of 94° C. for 30 seconds, 55° C. for 30 seconds and 72° C. for 30 seconds (35 cycles). A GC melt reagent (Clontech) at recommended dilution was always used in PCR reactions.

DNA sequencing was performed with ABI Prism dye termination DNA sequencing reagents (Perkin Elmer, Branchburg, N.J.) and an automated sequencing apparatus (Applied Biosystems ABI377 DNA Sequencer). DNA and protein sequence comparisons were performed with DNA* software from DNAstar Inc., Madison, Wis.

Example 1

Identification and Characterization of Human RCE

Yeast RCE1 amino acid sequence was used to query dbEST databases. Partial cDNAs for the human homolog of yeast RCE was found from dbEST [W96411 (p=2e-19); human and AA168614 (p=2e-10 20); mouse]. We obtained a human RCE homolog clone (358628) from the IMAGE Consortium, and sequenced it to confirm its homology to yeast RCE.

Northern analysis was performed to determine tissue distribution of human RCE using IMAGE clone 358628 as the probe. RCE expression appeared highest in placenta, with a transcript size of approximately 2.0 Kb. A human placenta phage library was screened to obtain a full length clone of human RCE. Six positive clones were found. Sequencing of these clones confirmed their homology to yeast RCE, IMAGE clone 358628, and to each other.

One of the positive clones, designated hRCE-7, was chosen for use in cloning and expression studies due to the presence of a start codon at the 5' end, a coding region containing a stop codon, and a 3' untranslated region including a poly $A^+$ tail. To demonstrate expression of human RCE, hRCE-7 was cloned into mammalian, bacterial, and yeast expression vectors. Epitope tags were cloned onto the amino and carboxy terminals of hRCE-7 for Western detection. The construct pDD1-hRCE containing the coding region of hRCE-7 with a 5' S-tag in a yeast expression vector was used to transform a yeast Rce/Afc double knock out, and the resulting yeast clone (136B) was positive in both Halo assay and biochemical assay.

The nucleotide sequence of the complete open reading frame and the corresponding amino acid sequence of human RCE cDNA cloned from the human placental cDNA library are defined in the Sequence Listing by SEQ ID NO: 1 and SEQ ID NO: 2, respectively.

Verification of Human RCE activity
Construction of Double Knockout Yeast Strain
RCE Knockout To construct the Rce knockout in yeast it is necessary to PCR amplify DNA containing a selectible marker (in this case HIS3) using PCR primers that 40 bps of yRCE sequence at the 5' end of the primers. These primers are called fusion primers because the 5' RCE sequence is fused to HIS3 sequences, which comprise the 3' end of the primer sequence. PCR amplification of the HIS3 gene with the fusion primers yielded a 1.0 kb DNA fragment. This is the correct size predicted for this amplification product. The amplification product contains the coding sequences for HIS3 and it contains yRCE sequences at the 5' and 3' ends.

When introduced into an appropriate yeast strain the yRCE sequences will direct the recombination of the PCR fragment into one of the alleles of the yRCE gene. This process disrupts the yRCE gene and places sequences encoding HIS3 at the yRCE locus.

For RCE disruption the 1.0 kb PCR product from the amplification described above was directly transformed into diploid histidine auxotroph BD 600 yeast strain (ade2/+ his3Δ200 leu2-3,112 trpl+ ura3-5). Yeast colonies able to grow in the absence of histidine (His +) were selected after transformation. The His+ diploid transformants were further screened for disruption of RCE by PCR methods. Diploids were sporulated to create haploid yeast strains and the haploid products of the sporulation were separated by dissection. The haploid strains were genetically characterized to identify a disruptant for RCE. One haploid that is ade2 minus (easy to select for red color), HIS positive and Mat α was selected and designated, IO2-c.

AFC1 Knockout

To construct the AFC1 knockout in yeast it is necessary to PCR amplify DNA containing a selectible marker (in this case LEU2) using PCR primers that 40 bps of yAFC sequence at the 5' end of the primers. These primers are called fusion primers because the 5' AFC sequence is fused to LEU2 sequences, which comprise the 3' end of the primer sequence. PCR amplification of the LEU2 gene with the fusion primers yielded a 1.5 kb DNA fragment. This is the correct size predicted for this amplification product. The amplification product contains the coding sequences for LEU2 and it contains yAFC1 sequences at the 5' and 3' ends.

When introduced into an appropriate yeast strain the yAFC1sequences will direct the recombination of the PCR fragment into one of the alleles of the yAFC gene. This process disrupts the yAFC gene and places sequences encoding LEU2 at the yAFC locus.

For AFC disruption the 1.5 kb PCR product from the amplification described above was directly transformed into haploid leucine auxotroph yeast strain BY4713(Mat Leu2Δ). Yeast colonies able to grow in the absence of leucine (Leu +) were selected after transformation. The Leu+haploid transformants were further screened for disruption of AFC1 by PCR methods. A clone designated, IO3-b, was selected. This strain was backcrossed to 1456 (Mat a,ho ade6 can1-100 his3-11,15 leu2-3,112 trpl-1 ura3-1) By crossing, dissection, and genetic analysis IO4-3b strain was selected because it is disrupted at the AFC1 locus and it is LEU+, URA–, HIS–, and mating type a. The Ura– and His– markers are necessary for constructing the AFC1/RCE1 double knockout strain by crossing the two single knockout strains. (for combining into the RCE/HIS3 locus).

The Double Knockout ΔRCE/ΔAFC

ΔRCE/ΔAFC knockout is the result of crossing Δ RCE IO2-c and ΔAFC IO4-3b. The two haploid strains are mated and the resulting diploids are selected in medium lacking leucine and histidine. The diploids are then sporulated and the resulting haploid spores are separated by dissection. The desired double knockout mutant is selected by its genetic characteristics. The strain should be His+, Leu+, Ura– and mat a. The final ACF1/RCE double knockout strain thus selected has a sterile phenotype due to the fact that it produces an immature a-factor protein. This strain can be used to test clones for RCE activity because RCE activity will restore the ability of this strain to mate.

Functional Complementation of RCE/AFC Double Knock Out Mutant

Levels of a-factor production were assayed by spotting samples of the cell suspension on a lawn of a-factor super-sensitive α sst2 cells. Released a-factor formed halos of growth-arrested MATα cells of sizes proportional to the amount of a-factor processing. Since Afc/Rce double knock out mutant is defective to process a-factor, human RCE gene we inserted to this mutant is responsible to cleave farnesylated a-factor enzymatically. The yeast clone (136B) was positive in Halo assay.

Biochemical Determination of Human RCE Activity

To measure RCE enzymatic activity, the tritiated K-ras peptide, Biotin-KKKSKTK-Cys(farnesyl)-[$^3$H]Val-Ile-Ser-COOH, was prepared as a substrate to detect RCE activity. This method employs Streptavidin beads for removing uncleaved or unreacted substrate peptide. The product released in the supernatant ([$^3$H]Val-Ile-Ser-COOH) was measured by scintillation counting and quantified. This method was used to detect human RCE activity after expression in Cos cells. We also inserted human RCE in yeast mutant (Afc/Rce K.O.) and detected human RCE activity in yeast membranes. Carbonate-leached membranes with hRCE showed endoprotease activity at a level of 0.6 nmol min$^{-1}$ mg$^{-1}$. Membranes prepared from a strain with yeast RCE give endoprotease activity of 3.7 nmol min$^{-1}$ mg$^{-1}$.

Example 3
Inhibitor Screening Assays
Transformation of hRCE

Yeast cells (IO10-16d; Rce/Afc double knock out) were grown at 30° C. in 10 ml YNB/gal/raff/ura$^-$ broth until early- to mid-log phase ( OD$_{600}$ of 0.4–0.8). Cells were centrifuged at 500 xg for 4 min and the supernatant discarded. After adding 10 ml EZ 1 solution (Zymo Research) to wash the pellet, the cells were again centrifuged and the supernatant removed. The cell pellet was then resuspended in 0.5–1 ml EZ 2 solution (Zymo Research). 50 μl of this competent cells was added to 0.2–0.5 μg human RCE DNA and 500 μl EZ 3 solution (Zymo Research) and mixed thoroughly. The mixture was incubated at 30° C. for 45 minutes during which time the mixture was vigorously vortexed 2–3 times. Following incubation, 50–150 μl of the above transformation mixture was spread on Ura$^-$ plates and incubated at 30° C. for 2–4 days to allow for growth of transformants.

Preparation of Yeast Membranes Containing Human RCE

Yeast cultures are grown in YNB/gal/raff/ura$^-$ medium at 30° C. to an OD$_{600}$ of 0.4–0.8. The cells are harvested by centrifugation at 5,000 g for 15 min at 4° C. and washed by resuspending the pellet in 200 ml chilled sterile water. The cell suspension is centrifuged as in the previous step and the cell pellet resuspended in 15 ml SST buffer [0.3 M sorbitol, 0.1 M NaCl, 10 mM Tris-HCl, pH 7.4, 5 mM EDTA, pH 8, containing 1x Complete Protease Inhibitor Cocktail (Boehringer Mannheim)]. The cells were lysed by three passes through a Microfluidizer (Nitrogen cavitation equipment). The cell lysate was centrifuged in a 15-ml Corex tube at 2,500 g for 20 min at 4° C. and the supernatant transferred to another 15-ml Corex tube. After adding ⅒ volume of 2M Na$_2$CO$_3$, pH 11.5, and mixing well, the lysate was Centrifuged at 100,000 g for 60 min at 4° C. After discarding the supernatant and gently washing the pellet in 2x5 ml cold SST buffer, the pellet was resuspended in 10 ml of cold SST buffer and homogenized by glass/Teflon homogenizer on ice. The sample was centrifuged again at 100,000 g for 60 min at 4° C. The pellet was resuspended in 2 ml of SST buffer and stored at –80° C. until use.

Direct Assay

2μg of membrane particulate was incubated in 100 μl of PBS (pH 7.4) with 500 pmol of synthetic radiolabeled peptide Biotin-KKKSKTKC(S-trans-trans-farnesyl)-[3,4-$^3$H-V]IS (24.4 mCi/mmol:Syn Pep) and 10 μg of bovine serum albumin (BSA) for 1 hour at 37° C. After incubation 30 μl of SPA beads (Streptavidin coated Scintillation Proximity Assay beads: Amersham) was added to pull-down of the unreacted substrate peptide. Following brief centrifugation to settle down beads, RCE activity was measured by scintillation counting of cleaved tripeptide ([$^3$H]Val-Ile-Ser-COOH) in the supernatant and quantified.

Coupled Assay:

The following is a protocol for a high-throughput Scintillation Proximity Assay (SPA) for inhibitors of human RCE. The method is a coupled RCE and prenyl cysteine-specific Carboxymethyltransferase (PC-CMT) assay. RCE first cleaves the farnesylated CaaX sequence of human K-Ras [Biotin-Ahx-SKTK-Cys(farnesyl)-VIM-COOH]. Subsequently, the peptide is methylated by PC-CMT which is present in the RCE membrane preparations, using [$^3$H]S-Adenosyl Methionine (SAM) as the methyl donor. [$^3$H] Methyl groups transferred to the farnesylated peptide substrate are quantified by binding to Streptavidin SPA beads and counting on a TopCount (or Microbeta).

5 μl of the diluted compound [20 μg/ml (10 x), 10% DMSO] to be tested for RCE inhibitor assay is transferred into each well of a 96-well Rigid Sample Plate. 5 μg human RCE (136B) membranes, 10 μl of 10 μM of substrate peptide [K-Ras peptide CS#8; Biotin-Ahx-SKTK-3 20 Cys (farnesyl)-VIM-COOH], 2 μl (500, 000 cpm) [$^3$H]S-Adenosyl-L-Methionine (hot SAM from NEN) and 2.5 μM cold SAM (Sigma) were added to the well. After addition of sufficient buffer to make 50 μl final volume, the plates were sealed with Wallac Sealing Tape and incubated on a shaker for 3 hrs at 37° C. The reaction was stopped by adding 200 μl of stop solution to every well. Stop solution was prepared so that 200 μl of stop solution contained 0.06% TX-100 and enough Streptavidin SPA beads (depending on the binding capacity of the lot, usually about 20 l of 500 mg/25 ml beads solution) to bind out 60 pmoles of substrate (20% excess).

Many modifications and variations of this invention can be made without departing from its spirit and scope, as will be apparent to those skilled in the art. The specific embodiments described herein are offered by way of example only, and the invention is to be limited only by the terms of the appended claims, together with the full scope of equivalents to which such claims are entitled.

What is claimed is:

1. A method for identifying an inhibitor of the endoprotease activity of human Ras Converting Endoprotease (RCE) having the amino acid sequence of SEQ ID NO: 2, said method comprising:
    (a) contacting a prenylated protein comprising a carboxy-terminal CaaX motif, wherein one or more of the three carboxy terminal amino acid residues of the prenylated protein is radiolabeled, with: (i) a sample to be tested for the presence of a RCE inhibitor; and (ii) human RCE having the amino acid sequence of SEQ ID NO: 2; and thereafter
    (b) measuring the amount of labeled tripeptide released, whereby the human RCE inhibitor in the sample is identified by measuring the substantially reduced release of the labeled tripeptide, compared to what would be measured in the absence of such inhibitor.

2. A method for identifying an inhibitor of the endoprotease activity of human Ras Converting Endoprotease (RCE) having the amino acid sequence of SEQ ID NO: 2, said method comprising:
    (a) contacting a prenylated peptide comprising a carboxy-terminal CaaX motif with: (i) a sample to be tested for the presence of a RCE inhibitor; (ii) human RCE having the amino acid sequence of SEQ ID NO: 2; (iii) prenyl cysteine specific carboxymethyltransferase; and (iv) a radiolabeled methyl group donor; and
    (b) measuring the amount of the radiolabeled methyl group incorporated into the carboxy terminal of the prenylated peptide
    whereby the human RCE inhibitor in the sample is identified by measuring the reduction in the amount of radiolabeled methyl group incorporated into the prenylated peptide, compared to what would be measured in the absence of such inhibitor.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1483 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Homo sapiens (ix) FEATURE:
         (A) NAME/KEY: CDS
         (B) LOCATION: 14..1000

(xi) SEQUENCE DESCRIPTION: SEQ ID NO:1:

```
GGATCCGCGC GCA ATG GCG GCG CTG GGC GGG GAT GGG CTG CGA CTG CTG         49
            Met Ala Ala Leu Gly Gly Asp Gly Leu Arg Leu Leu
              1               5                  10

TCG GTG TCG CGG CCG CAG CGG CCG CCC GAG TCG GCG GCG CTG GGC GGC         97
Ser Val Ser Arg Pro Gln Arg Pro Pro Glu Ser Ala Ala Leu Gly Gly
             15                  20                  25

CTG GGC CCC GGG CTG TGC TGC TGG GTG TCA GTG TTC TCC TGC CTC AGC        145
Leu Gly Pro Gly Leu Cys Cys Trp Val Ser Val Phe Ser Cys Leu Ser
 30                  35                  40

CTC GCC TGC TCC TAT GTG GGC AGC CTC TAC GTC TGG AAG AGC GAA CTG        193
Leu Ala Cys Ser Tyr Val Gly Ser Leu Tyr Val Trp Lys Ser Glu Leu
 45                  50                  55                  60

CCC AGG GAC CAT CCC GCG GTC ATC AAG CGA CGC TTC ACC AGC GTC CTG        241
Pro Arg Asp His Pro Ala Val Ile Lys Arg Arg Phe Thr Ser Val Leu
                 65                  70                  75

GTG GTG TCC AGT CTC TCA CCC CTG TGC GTG CTG CTC TGG AGG GAA CTC        289
Val Val Ser Ser Leu Ser Pro Leu Cys Val Leu Leu Trp Arg Glu Leu
                 80                  85                  90

ACA GGC ATC CAG CCA GGC ACA TCC CTG CTC ACC CTG ATG GGC TTC AGG        337
Thr Gly Ile Gln Pro Gly Thr Ser Leu Leu Thr Leu Met Gly Phe Arg
             95                 100                 105

CTG GAG GGC ATT TTC CTA GCG GCG CTG CTG CCC CTG TTG CTG ACC ATG        385
Leu Glu Gly Ile Phe Leu Ala Ala Leu Leu Pro Leu Leu Leu Thr Met
    110                 115                 120

ATT CTT TTC CTG GGC CCA CTG ATG CAG CTC TCT ATG GAT TGC CCT TGT        433
Ile Leu Phe Leu Gly Pro Leu Met Gln Leu Ser Met Asp Cys Pro Cys
125                 130                 135                 140

GAC CTG GCA GAT GGG CTG AAG GTT GTC CTG GCC CCC CGC TCC TGG GCC        481
Asp Leu Ala Asp Gly Leu Lys Val Val Leu Ala Pro Arg Ser Trp Ala
                145                 150                 155

CGC TGC CTC ACA GAC ATG CGT TGG CTG CGG AAC CAA GTG ATC GCC CCG        529
Arg Cys Leu Thr Asp Met Arg Trp Leu Arg Asn Gln Val Ile Ala Pro
            160                 165                 170

CTG ACA GAG GAG CTG GTG TTC CGG GCC TGT ATG CTG CCC ATG TTA GCA        577
Leu Thr Glu Glu Leu Val Phe Arg Ala Cys Met Leu Pro Met Leu Ala
        175                 180                 185

CCG TGC ATG GGC CTG GGC CCT GCT GTG TTC ACC TGC CCG CTC TTT TTT        625
Pro Cys Met Gly Leu Gly Pro Ala Val Phe Thr Cys Pro Leu Phe Phe
    190                 195                 200

GGA GTT GCC CAT TTT CAC CAT ATT ATT GAG CAG CTG CGT TTC CGC CAG        673
Gly Val Ala His Phe His His Ile Ile Glu Gln Leu Arg Phe Arg Gln
205                 210                 215                 220

AGC AGC GTG GGG AAC ATC TTC TTG TCT GCT GCG TTC CAG TTC TCC TAC        721
Ser Ser Val Gly Asn Ile Phe Leu Ser Ala Ala Phe Gln Phe Ser Tyr
                225                 230                 235

ACA GCT GTC TTC GGT GCC TAC ACT GCT TTC CTC TTC ATC CGC ACA GGA        769
Thr Ala Val Phe Gly Ala Tyr Thr Ala Phe Leu Phe Ile Arg Thr Gly
            240                 245                 250
```

```
CAC CTG ATT GGG CCG GTT CTC TGC CAT TCC TTC TGC AAT TAC ATG GGT      817
His Leu Ile Gly Pro Val Leu Cys His Ser Phe Cys Asn Tyr Met Gly
        255                 260                 265

TTC CCA GCT GTT TGC GCG GCC TTG GAG CAC CCA CAG AGG CGG CCC CTG      865
Phe Pro Ala Val Cys Ala Ala Leu Glu His Pro Gln Arg Arg Pro Leu
        270                 275                 280

CTG GCA GGC TAT GCC CTG GGT GTG GGA CTC TTC CTG CTT CTG CTC CAG      913
Leu Ala Gly Tyr Ala Leu Gly Val Gly Leu Phe Leu Leu Leu Leu Gln
285                 290                 295                 300

CCC CTC ACG GAC CCC AAG CTC TAC GGC AGC CTT CCC CTT TGT GTG CTT      961
Pro Leu Thr Asp Pro Lys Leu Tyr Gly Ser Leu Pro Leu Cys Val Leu
            305                 310                 315

TTG GAG CGG GCA GGG GAC TCA GAG GCT CCC CTG TGC TCC TGACCTATGC      1010
Leu Glu Arg Ala Gly Asp Ser Glu Ala Pro Leu Cys Ser
            320                 325

TCCTGGATAC GCTATGAACT CTCACCGGCT CCCCAGCCCT CCCCACCAAG GGGTACTGCA   1070

GGGGAAGGGC TGGCTGGGGT CCCCGAGATC TCAGGAATTT TTGTAGGGGA TTGAAGCCAG   1130

AGCTAGTTGC GTCCCAGGGA CCAAGAGAAA GAAGCAGATA TCCAAAGGGT GCAGCCCCTT   1190

TTGAAAGGGG TGTTTACGAG CAGCTGTGAG TGAGGGGACA AGGGGCAAGG TCCCAGGAGC   1250

CACACACTCC CTTCCTCACT TTGGACTGCT GCTTCTCTTA GCTCCTCTGC CTCTGAAAAG   1310

CTGCTCGGGG TTTTTTATTT ATAAAACCTC TCCCCACCCC CCACCCCCCA ACTTCCTGGG   1370

TTTTCTCATT GTCTTTTTGC ATCAGTACTT TGTATTGGGA TATTAAAGAG ATTTAACTTG   1430

GGTAAAAAAA AAAAAAAAAA AAAAAAAAAA AAAAAAAAAA AAAAAAAAAA AAA          1483

(2) INFORMATION FOR SEQ ID NO:2:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ala Leu Gly Gly Asp Gly Leu Arg Leu Leu Ser Val Ser Arg
1               5                   10                  15

Pro Gln Arg Pro Glu Ser Ala Ala Leu Gly Leu Gly Pro Gly
            20                  25                  30

Leu Cys Cys Trp Val Ser Val Phe Ser Cys Leu Ser Leu Ala Cys Ser
            35                  40                  45

Tyr Val Gly Ser Leu Tyr Val Trp Lys Ser Glu Leu Pro Arg Asp His
        50                  55                  60

Pro Ala Val Ile Lys Arg Arg Phe Thr Ser Val Leu Val Ser Ser
65                  70                  75                  80

Leu Ser Pro Leu Cys Val Leu Leu Trp Arg Glu Leu Thr Gly Ile Gln
                85                  90                  95

Pro Gly Thr Ser Leu Leu Thr Leu Met Gly Phe Arg Leu Glu Gly Ile
            100                 105                 110

Phe Leu Ala Ala Leu Leu Pro Leu Leu Leu Thr Met Ile Leu Phe Leu
            115                 120                 125

Gly Pro Leu Met Gln Leu Ser Met Asp Cys Pro Cys Asp Leu Ala Asp
        130                 135                 140

Gly Leu Lys Val Val Leu Ala Pro Arg Ser Trp Ala Arg Cys Leu Thr
145                 150                 155                 160

Asp Met Arg Trp Leu Arg Asn Gln Val Ile Ala Pro Leu Thr Glu Glu
```

-continued

```
                165                    170                    175
Leu Val Phe Arg Ala Cys Met Leu Pro Met Leu Ala Pro Cys Met Gly
            180                185                190

Leu Gly Pro Ala Val Phe Thr Cys Pro Leu Phe Phe Gly Val Ala His
        195                200                205

Phe His His Ile Ile Glu Gln Leu Arg Phe Arg Gln Ser Ser Val Gly
    210                215                220

Asn Ile Phe Leu Ser Ala Ala Phe Gln Phe Ser Tyr Thr Ala Val Phe
225                230                235                240

Gly Ala Tyr Thr Ala Phe Leu Phe Ile Arg Thr Gly His Leu Ile Gly
                245                250                255

Pro Val Leu Cys His Ser Phe Cys Asn Tyr Met Gly Phe Pro Ala Val
            260                265                270

Cys Ala Ala Leu Glu His Pro Gln Arg Arg Pro Leu Leu Ala Gly Tyr
            275                280                285

Ala Leu Gly Val Gly Leu Phe Leu Leu Leu Gln Pro Leu Thr Asp
    290                295                300

Pro Lys Leu Tyr Gly Ser Leu Pro Leu Cys Val Leu Leu Glu Arg Ala
305                310                315                320

Gly Asp Ser Glu Ala Pro Leu Cys Ser
                325
```